United States Patent
Burke, JR. et al.

(10) Patent No.: US 9,361,780 B2
(45) Date of Patent: Jun. 7, 2016

(54) DEVICE AND METHOD FOR RECORDING AND TRANSMITTING INTERVAL DATA FROM A CONTAINER CAP

(71) Applicant: Timer Cap Company, LLC, Thousand Oaks, CA (US)

(72) Inventors: Richard Million Burke, JR., Westlake Village, CA (US); Howard David Goldberg, Westlake Village, CA (US); Philip John Tomasi, Newbury Park, CA (US); Lawrence M. Twersky, Tarzana, CA (US)

(73) Assignee: TimerCap, LLC, Tarzana, CA (US)

( * ) Notice: Subject to any disclaimer, the term of this patent is extended or adjusted under 35 U.S.C. 154(b) by 356 days.

(21) Appl. No.: 13/828,919

(22) Filed: Mar. 14, 2013

(65) Prior Publication Data

US 2014/0266760 A1    Sep. 18, 2014

Related U.S. Application Data

(63) Continuation-in-part of application No. 13/038,331, filed on Mar. 1, 2011, now abandoned, and a continuation-in-part of application No. 13/244,269, filed on Sep. 23, 2011, now Pat. No. 9,129,098.

(51) Int. Cl.
| | |
|---|---|
| *G08B 1/00* | (2006.01) |
| *G08B 23/00* | (2006.01) |
| *G08B 21/24* | (2006.01) |
| *G06F 19/00* | (2011.01) |

(52) U.S. Cl.
CPC ............ *G08B 21/24* (2013.01); *G06F 19/3462* (2013.01)

(58) Field of Classification Search
None
See application file for complete search history.

(56) References Cited

U.S. PATENT DOCUMENTS

| | | |
|---|---|---|
| 2,961,108 A | 11/1960 | Johnson |
| 4,261,656 A | 4/1981 | Wu |
| 4,367,955 A | 1/1983 | Ballew |
| D295,024 S | 4/1988 | Trick |
| 4,826,914 A | 5/1989 | Raedisch |
| 5,014,798 A | 5/1991 | Glynn |
| 5,030,686 A | 7/1991 | Holzer |
| 5,216,975 A | 6/1993 | Bartholomew |
| 5,233,571 A | 8/1993 | Wirtschafter |
| 5,268,136 A | 12/1993 | Girard |
| RE34,523 E | 1/1994 | Daude |
| 5,313,439 A | 5/1994 | Albeck |
| 5,334,178 A | 8/1994 | Haber |
| 5,386,795 A | 2/1995 | Bartholomew |

(Continued)

FOREIGN PATENT DOCUMENTS

| | | |
|---|---|---|
| CN | 1498829 | 5/2004 |
| WO | 2007011656 | 1/2007 |
| WO | 2007011656 | 6/2007 |

*Primary Examiner* — Benjamin C Lee
*Assistant Examiner* — Chico A Foxx
(74) *Attorney, Agent, or Firm* — Hankin Patent Law, APC

(57) ABSTRACT

The present invention is a container cap sensors, chips, transmitters, and receiver, to record, transmit, and receive data regarding the time intervals between when the container cap was last placed on or taken off of a container. The container cap is for use with pharmaceutical and other health care related vials, bottles and containers. The data transmission is used to monitor a patient's drug administration times and intervals, and allows the patient and/or the patient's caregiver to review the administration data. The container cap of the present invention is streamlined, easy to use, reliable, and inexpensive.

4 Claims, 7 Drawing Sheets

(56) References Cited

U.S. PATENT DOCUMENTS

| | | |
|---|---|---|
| 5,720,392 A | 2/1998 | Price |
| 5,798,409 A | 8/1998 | Ho |
| 6,084,504 A | 7/2000 | Rosche et al. |
| 6,229,431 B1 | 5/2001 | Weiner |
| 6,317,390 B1 | 11/2001 | Cardoza |
| 6,324,123 B1 | 11/2001 | Durso |
| 6,373,786 B1 | 4/2002 | Kagan et al. |
| 6,424,599 B1 | 7/2002 | Ditzig |
| 6,604,650 B2 | 8/2003 | Sagar |
| 6,667,936 B1 | 12/2003 | Ditzig |
| 6,707,763 B2 | 3/2004 | Osberh et al. |
| 6,845,064 B2 | 1/2005 | Hildebrandt |
| 7,081,807 B2 | 7/2006 | Lai |
| D550,571 S | 9/2007 | Diaz |
| 7,339,457 B2 | 3/2008 | Trochesset |
| 7,362,660 B2 | 4/2008 | Hildebrandt |
| 7,382,692 B1 | 6/2008 | Hildebrandt |
| 7,405,647 B2 | 7/2008 | Rosche et al. |
| 7,408,843 B2 * | 8/2008 | Brandon ............... A61J 7/0472 215/329 |
| 7,680,001 B1 * | 3/2010 | D'Annunzio ........... B65D 51/20 215/247 |
| 7,719,927 B1 | 5/2010 | Robinson et al. |
| 7,796,472 B2 | 9/2010 | Brandon |
| 7,907,477 B2 * | 3/2011 | Puzia .................. A61J 7/0472 215/230 |
| 7,928,835 B1 | 4/2011 | Jovanov |
| 8,045,420 B2 | 10/2011 | Newman |
| 8,391,104 B2 * | 3/2013 | de la Huerga ........... A61J 1/035 206/459.5 |
| 8,441,893 B2 * | 5/2013 | Stauffer ................. G04F 10/00 368/10 |
| 8,727,180 B2 * | 5/2014 | Zonana ............. B65D 83/0409 221/195 |
| 8,823,510 B2 * | 9/2014 | Downey ................ A61J 1/1412 215/228 |
| 8,842,501 B2 * | 9/2014 | Ziemba .................. G04B 47/00 368/109 |
| 2002/0126585 A1 * | 9/2002 | Osberg et al. ................. 368/107 |
| 2003/0099158 A1 * | 5/2003 | De la Huerga .................. 368/10 |
| 2003/0198134 A1 | 10/2003 | Hildebrandt |
| 2005/0121407 A1 | 6/2005 | Hildebrandt |
| 2005/0151625 A1 | 7/2005 | Lai |
| 2006/0154642 A1 * | 7/2006 | Scannell ................. A01G 9/02 455/404.1 |
| 2006/0218011 A1 * | 9/2006 | Walker et al. ...................... 705/3 |
| 2007/0014191 A1 * | 1/2007 | Brandon ............... A61J 7/0472 368/10 |
| 2008/0114490 A1 * | 5/2008 | Jean-Pierre ................... 700/241 |
| 2009/0078670 A1 | 3/2009 | Brandon |
| 2010/0142330 A1 | 6/2010 | Reygaert |
| 2010/0271224 A1 * | 10/2010 | Varasteh ....................... 340/644 |
| 2011/0069587 A1 | 3/2011 | Brandon |
| 2011/0119090 A1 * | 5/2011 | Lazar .............................. 705/3 |
| 2011/0216627 A1 | 9/2011 | Ziemba |
| 2011/0273280 A1 | 11/2011 | Chang et al. |
| 2012/0160908 A1 | 6/2012 | Downey et al. |
| 2012/0161929 A1 | 6/2012 | Downey et al. |
| 2012/0163132 A1 | 6/2012 | Downey et al. |
| 2012/0187142 A1 | 7/2012 | Flowers et al. |
| 2012/0223045 A1 | 9/2012 | Burke |
| 2012/0224458 A1 | 9/2012 | Burke, Jr. |
| 2012/0239419 A1 | 9/2012 | Allen |
| 2012/0257478 A1 | 10/2012 | Marcellino |
| 2012/0319856 A1 | 12/2012 | Johnson |
| 2013/0002429 A1 | 1/2013 | Johnson |
| 2014/0055267 A1 * | 2/2014 | Rothschild ................... 340/573.1 |
| 2014/0188502 A1 * | 7/2014 | Defrank et al. .................... 705/2 |
| 2014/0251850 A1 * | 9/2014 | Huang et al. ................ 206/459.1 |

* cited by examiner

DEVICE AND METHOD FOR RECORDING AND TRANSMITTING INTERVAL DATA FROM A CONTAINER CAP

CROSS-REFERENCE TO RELATED APPLICATIONS

This application is a Continuation-in-Part application to U.S. Non-Provisional patent application Ser. No. 13/038,331, filed on Mar. 1, 2011, titled "CONTAINER CAP WITH PROTECTIVE COVER" by inventor Richard Million Burke, Jr., and to U.S. Non-Provisional patent application Ser. No. 13/244,296, filed on Sep. 24, 2011, titled "CONTAINER CAP WITH A TIMER" by inventor Richard Million Burke Jr., the contents of which are both expressly incorporated herein by this reference, and to which priority is claimed.

FIELD OF INVENTION

The present invention generally relates to container caps, and, more particularly, to container caps with sensors, chips, transmitters, and receivers, to record, transmit, and receive data regarding when the container cap was last placed on or taken off of a container. The preferred use of the container cap of the present invention is for use with vials, bottles or containers containing pharmaceuticals, over-the-counter (OTC) medications, nutraceuticals or other goods for both human and animal consumption.

BACKGROUND

Modern health care practice relies on patients to consistently take their medications, nutraceuticals and supplements at one or more specific intervals during the day and to accurately record or remember each time a dose was taken. Typically, the patient's doctor will create a medication schedule for the patient and instruct the patient to follow the schedule. However, with changes in medications and their dosing schedules or when the patient has multiple medications that may be taken at different times, the schedule can quickly become complex and unwieldy.

In an effort to simplify medication schedules and keep better track of when a particular medication was last taken, various products and methods have been developed. One approach was to build a timer into a bottle cap, to indicate the last time the bottle was opened, helping the patient to easily see when their last dosage was taken by looking at the timer. This solution only allows for a single or short term display of when the bottle was last opened or closed.

It is currently estimated that in developed countries such as the U.S. less than 50% of the medications prescribed are taken as directed. Poor medication adherence, or failure to comply with medication dosage instructions, results in more than 125,000 deaths, 1.5 million injuries and $300 Billion in increased health care costs annually in the U.S. alone. The reasons for these injuries and deaths range from underdoses and overdoses, interactions between drugs, errors dispensing or administering drugs, failure to take drugs as directed due to forgetfulness, or due to poor monitoring of patients on medication.

Additionally, some people cannot be trusted with unmonitored access to various drugs because they may lack the self-control or adequate presence of mind to know when and how to properly take their medication.

It is impractical to have a qualified physician or health professional be present at each drug administration due to the billions of prescriptions prescribed each year. Also, manually keeping track of one's drug regimens for review by a qualified physician is not practical for most busy people, and the record is effectively worthless unless each and every administration is tracked and recorded. Manually tracking drug administration is simply not a reliable solution.

When dealing with today's highly effective prescription drugs, even minor discrepancies between when a drug was administered and what the recorded administration time shows, may have significant impact. Leaving the patient be in charge of that record keeping is almost certain to result in discrepancies.

Various products and methods have been developed in order to simplify medication schedules and keep better track of when a particular medication was last taken. U.S. Pat. No. 6,424,599 issued to Ditzig, discloses a disposable bottle cap reminder device with an electronic counter that counts time when activated and resets time when deactivated. The electronic counter is connected to a battery and switching mechanism is comprised of a conductive contact spring in conductive contact with the power source and a conductive plate. While this disclosure teaches how to detect whether a bottle cap has been opened, as many other references have, it does so only by counting the time since the last time the container was opened, which fails to place that information into a format which can be compiled and transmitted quickly and easily.

U.S. Pat. No. 6,604,650, issued to Sagar, discloses a medicine dispensing system that has a timer and informs the user as to whether or when to take a next medication dose. A communications interface enables programming of a parameter associated with administering a medication. Importantly, the functionality of this device is limited to detecting whether a dose of medication has been taken, and reminding a user to take medication through receipt of a signal from a sensor.

U.S. Published Patent Application No. (USPPN) 2012/0163132, filed by Downey, discloses a system and method for wirelessly programming a prescription bottle cap. The system includes a base station comprising an inductor and processor configured to receive instructions, which may then be transferred to the prescription bottle cap via the use of an inductor to alter the magnetic field of the prescription bottle cap to reflect the newer dosage. Importantly, this reference merely discloses how to send and program reminders into a prescription bottle cap, and fails to offer the user a method of monitoring and transmitting data regarding actual drug administration.

USPPN 2012/0187142, filed by Flowers, discloses a bottle cap which is capable of transmitting data related to precise time data regarding when a cap was opened and closed with respect to a container with multiple chambers. Flowers focuses entirely on a multi-chamber container and when each chamber was opened, and utterly fails to disclose recording interval data from a container with a single chamber.

U.S. Pat. No. 6,707,763, issued to Osberg, and concurrently owned with the present invention, discloses a pharmaceutical bottle timer cap that informs the user how long it has been since the medication in the bottle was taken. The Osberg timer cap automatically starts the timer when the cap is replaced on the bottle after the medication has been taken. The Osberg timer cap has no way to automatically record and send measurements and data to be used or viewed elsewhere at a later time.

Simply put, before the present invention, transmitting wireless information regarding container cap opening and closing interval data has never been disclosed, taught, or suggested by any reference. Thus, what is needed is a container cap with a chip, transmitter, and receiver that automatically collects and sends interval data or information to be further processed and interpreted at a later time using an external computer or other type of electronic data processing unit.

SUMMARY OF THE INVENTION

To minimize the limitations in the prior art, and to minimize other limitations that will become apparent upon reading and understanding the present specification, the present invention is a container cap that records and transmits data regarding the duration of time intervals between the opening and closing of the container cap to a container. The container cap may also have a timer and a timer display that shows the user a plurality of information, such as when the container was last closed. The timer cap of the present invention is streamlined, easy to use, reliable, and inexpensive.

One embodiment of the invention is a container cap that records and transmits data comprising: a container cap; wherein the container cap is comprised of: one or more sensors; one or more microcontrollers; one or more transmitters; one or more power sources; and a housing portion. The one or more sensors are configured to automatically detect when the container cap is removed from a container and wherein the one or more sensors are configured to automatically detect when the container cap is placed on the container. The one or more microcontrollers record when the container cap is opened by removing the container cap from the container and wherein the one or more microcontrollers record when the container cap is closed by placing the container cap on the container, as well was the duration of intervals between when the container cap is closed by placing the container cap on the container and wherein the one or more microcontrollers record when the container caps is opened by removing the container cap from the container, such that a plurality of opening and closing data is created and stored in at least one memory. It should be understood that the phrases "container cap is opened" and "container cap is closed" refer to the container cap being secured to (or placed on) or removed from a container. These phrases do not refer to the container cap itself being broken open or fitted together to itself. The one or more transmitters transmits the plurality of opening and closing data to one or more external electronic data processing units. Preferably, the container cap further comprises a timer and a timer display. The timer recording closed event intervals is preferably actuated when the container cap is closed and the event interval timer is deactivated or reset when the container cap is opened. The timer display preferably displays information regarding when the container cap was last closed. Preferably, a plurality of interval time duration data between a closing event and a next subsequent opening event as well as between an opening event and a next subsequent closing event is computed by the one or more microcontrollers each time the container cap is opened and/or closed and wherein the plurality of interval time duration data is stored in the at least one memory. A closing event is generally when the container cap is closed or put onto a container. An opening event is generally when the container cap is opened or removed from the container. Preferably, the plurality of interval time duration data is transmitted by the one or more transmitters to the one or more external electronic data processing units. Preferably, the container cap is further comprised of: one or more receivers; wherein the one or more receivers are configured to receive a plurality of transmissions from the one or more external electronic data processing units. Alternatively, the transmitters and receivers may be combined as one or more transceivers. Preferably, at least one of the one or more sensors is an accelerometer, which senses when or how the container cap is moved. The accelerometer can sense the force by which a cap was moved, setting a threshold, as well as if it was turned upside down or in other ways. Preferably, the one or more microcontrollers send an identification data to the one or more electronic data processing units. This way the electronic data processing unit knows which cap is which. Preferably, the at least one of the one or more sensors is a thermometer and the one or more microcontrollers records a plurality of temperature data from the thermometer. Preferably, the plurality of temperature data is transmitted by the one or more transmitters or transceivers to the one or more external electronic data processing units. Preferably, the container cap is further comprised of one or more alert devices, such as one or more light sources; a speaker; and a vibration device. The alert devices alert a user regarding one or more reminders or one or more conditions regarding the container cap. The plurality of interval time duration data and the plurality of opening and closing data that are transmitted to the one or more external electronic data processing units may be encrypted. The memory may be within or part of the microcontrollers. Or the memory or memory units may be separate devices. Preferably, the timer display further displays the information selected from the information consisting of: a name of a product contained within the container; a patient name; the frequency of which a medication should be taken; a number of times the container cap was opened over a set duration; the next scheduled time to take the medication; an advertisement; a warning; a most recent interval; and a reorder information.

Another embodiment of the device is a container cap that records and transmits data comprising: a container cap; wherein the container cap is comprised of: one or more sensors; one or more microcontrollers; one or more transceivers; one or more power sources; a timer; a timer display; and a housing portion. The one or more sensors are configured to automatically detect when the container cap is removed from a container and wherein the one or more sensors are configured to automatically detect when the container cap is placed on the container, and the one or more microcontrollers record when the container cap is opened by removing the container cap from the container and wherein the one or more microcontrollers record when the container cap is closed by placing the container cap on the container, such that a plurality of interval duration data between closing and opening events as well as opening and closing events is created and stored in at least one memory. The closed event interval timer is actuated when the container cap is closed and when the container cap is opened the event interval timer is deactivated. The timer display displays an information regarding when the container cap was last placed on the container. A plurality of interval time duration data between a closing event and a next subsequent opening event, as well as the time duration data of how long the container cap was left open or off the container, is computed by the one or more microcontrollers each time the container cap is opened and wherein the plurality of interval time duration data is stored in the at least one memory; and the one or more transceivers transmits the plurality of opening and closing data and the plurality of interval time duration data to one or more external electronic data processing units. Preferably, the one or more transceivers are configured to receive a plurality of transmissions from the one or more external electronic data processing units. Preferably, the at least one of the one or more sensors is an accelerometer, which senses when and how the container cap is moved.

Preferably the power source is a battery, but it may be a solar panel, a kinetic motion based electricity generator, AC power source, or any other type of electricity or power generator.

In alternate embodiments, the one or more sensors may take other measurements, such as weight, volume, pH, temperature, movement, acceleration, humidity, pressure, magnetic fields, gravity, moisture, vibration, electrical fields, sounds, and gasses. These measurements may then be transmitted to the electronic data processing unit for further analysis, review, and processing.

In another embodiment of the invention, a method for monitoring and recording drug administration is made available. This is preferably done by providing a container cap which can transmit a signal upon request, movement, opening, or closing through a radio frequency transmitter to an electronic data processing unit configured to receive the signal in order to collect and process the data provided by the container cap. The data preferably includes the length of time (or interval) over which the container cap was closed and then opened as well as data of the length of time intervals measuring how long the container remained open.

It is an object of the invention to allow recordation of data and events without the manual input of a user. This recordation of data would be available in an easily sharable digital format.

It is another object of the invention to be inexpensive enough to be disposable, thereby reducing dangers of cross contamination. Yet the container cap is preferably durable enough such that it could be reusable for long periods of time if there is no danger of cross contamination.

It is another object of the invention to work with commonly available types of containers.

It is another object of the invention to allow the device to function regardless of travel between time zones. That is, because an object of an embodiment of the current invention records and transmits the relative references via data strings that convey the duration of intervals between events from which specific times are then calculated rather than transmitting specific time references, a patient who is traveling between time zones where the electronic data processing unit has different times is still able to accurately gauge their medication use.

It is an object of this invention to overcome the limitations of the prior art.

Other features and advantages are inherent in the container cap with a timer as claimed and disclosed will become apparent to those skilled in the art from the following detailed description and its accompanying drawings.

BRIEF DESCRIPTIONS OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION OF THE DRAWINGS

Figure 1:
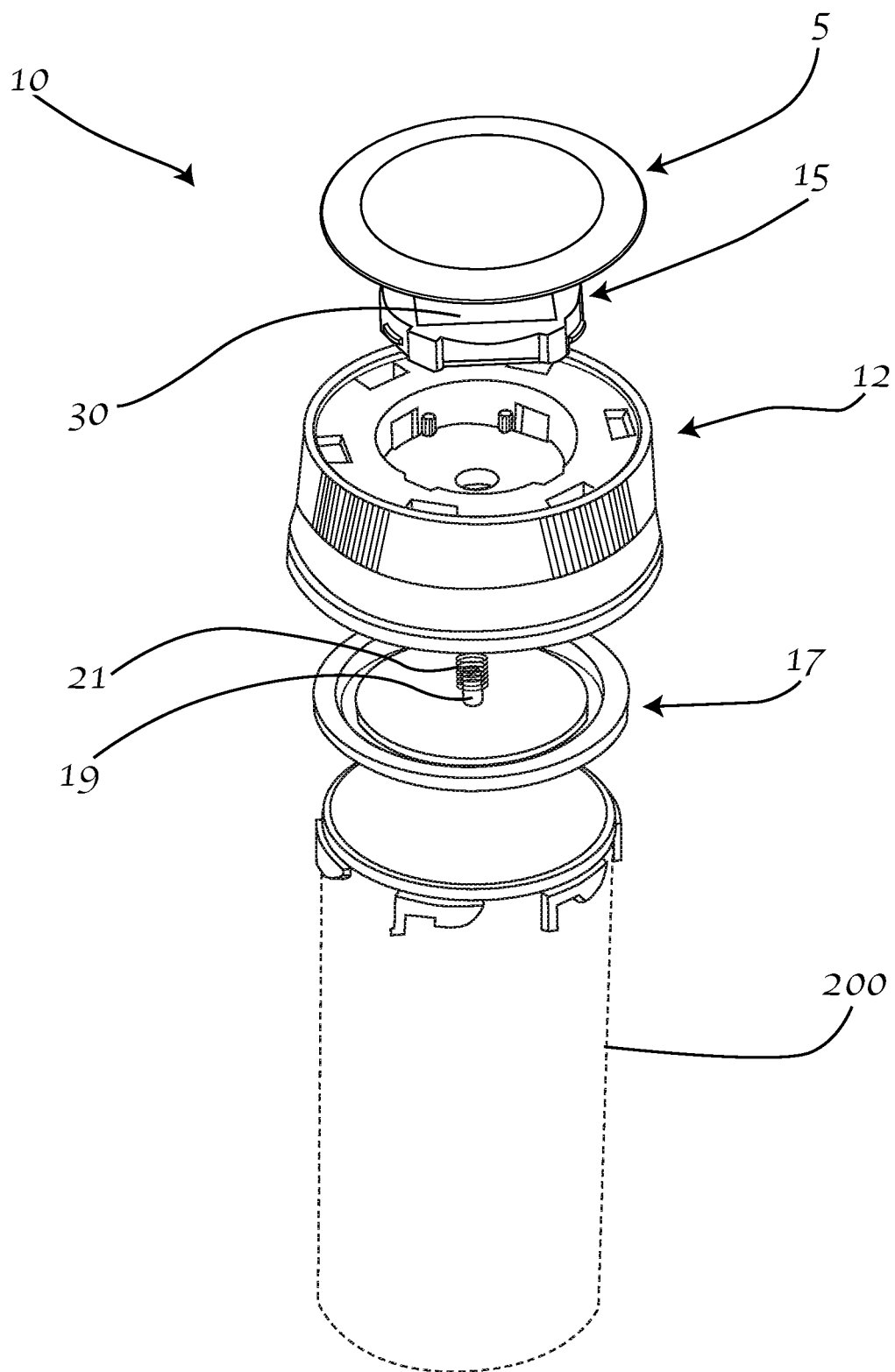
FIG. 1 is an illustration of a top exploded view of one embodiment of a container cap that records and transmits data.

In the following detailed description of the preferred embodiment, reference is made to the accompanying drawings that form a part hereof, and in which is shown, by way of illustration, a specific embodiment in which the invention may be practiced. It is to be understood that other embodiments may be utilized and structural changes may be made without departing from the scope of the present invention.

In the following detailed description of various embodiments of the invention, numerous specific details are set forth in order to provide a thorough understanding of various aspects of one or more embodiments of the invention. However, one or more embodiments of the invention may be practiced without these specific details. In other instances, well-known methods, procedures, and/or components have not been described in detail so as not to unnecessarily obscure aspects of embodiments of the invention.

In the following description, certain terminology is used to describe certain features of one or more embodiments of the invention. The term "container cap" refers to a lid, cap, top, topper, bung, stopper, cover, tap, seal, or closure of a container, vial or bottle. The cap and container are preferably a pharmaceutical prescription safety cap and a pharmaceutical prescription bottle or vial, but they may be any cap or container without deviating from the scope of the invention, including those used for the packaging of over-the-counter medications, nutraceuticals, and pet medications. Additionally, "computer" or "electronic data processing unit" refers to any electronic data processing unit or device that processes information with an integrated circuit chip, including without limitation, mainframe computers, work stations, servers, desktop computers, portable computers, laptop computers, embedded computers, wireless devices including cellular phones, smart phones, personal digital assistants, personal health monitoring devices, portable game players, and handheld computers.

The container cap is typically made of plastic or some other synthetic material, but any natural or man-made material may be used.

To achieve the functionality described herein, the container cap of the present invention preferably includes at least one sensor (or switch), which activates the timer and determines that the container cap is placed on or removed from the container. The preferred switch is described in U.S. patent application Ser. No. 13/244,296, which is a centrally activated switch. The container cap may also include:

(1) a receiver (which may include an antenna);
(2) a battery (or other power source);
(3) a circuit board (to hold the microcontroller and to connect the various digital electronic components, including the sensors, displays, drivers, memory units, and timer);
(4) displays (preferably digital);

(5) display drivers (which may or may not be part of the microcontroller);
(6) a housing (or enclosure, to protect and hold all of the delicate components of the container cap);
(7) the microcontroller (which is preferably is a very small (micro) computer on a single integrated circuit containing, preferably, a processor core, memory, and programmable input/output peripherals, which runs on-board programs and may or may not store the programs);
(8) additional memory (in addition to a memory that may or may not be part of the microcontroller);
(9) a transmitter or transceiver (such as radio transmitter, a radio-frequency identification (RFID), Bluetooth, Near Field communication, and the like);
(10) software (preferably embedded into the microcontroller); and
(11) additional components, such as sensors (accelerometers, thermometers, scales, weight measuring devices, volume measuring devices, pH sensors, movement, humidity sensors, magnetic field sensors, gravity sensors, vibration sensors, radiation sensors, electromagnetic sensors, microphones and other sound sensors, and the like), and output or alert devices (one or more light sources, speakers (or tone generators to buzz or make an audible noise), and vibration generators). The one or more light sources may be used, via color shifting or strobing, to: a) identify one user/owner from another; b) alert the owner to a pending event, such as the time to take a medication has arrived or passed; and/or c) warn the user of a condition requiring attention, such as the fact that the medication has been stored outside prescribed temperature range, or it is time to reorder, etc.

Preferably, the external electronic data processing unit (or computer) that communicates with the container cap is a smart phone, tablet computer, lap top computer, dedicated computing device, personal health monitoring device, and/or desktop computer. This external computer preferably includes software that allows it to communicate with the container cap. Data collected by the container cap may be requested by the external computer, or the data may be automatically sent by the container cap once a recognition hand shake has been established between the container cap and external computer.

The external computer may have the following features and capabilities: locate the container cap via signal strength; send data and commands; receive data, current or historical; identify specific container caps from other similar container caps; purge or reset information saved on the microcontroller; "pattern match" historical data downloaded from the container cap and append only the new data to previously received data, so as to prevent duplication and confusion; calculate specific opening and closing times from data intervals, identify temperature extremes that might have a deleterious effect on the performance of the substances within the container; determine the number of times a container was accessed and determine if the substance within the container needs to be reordered; collect feedback from a user regarding a user's responses to the medication, including any side effects; reorder medications; and/or place an emergency call for help.

For container caps that include a receiver or transceiver, the external computer could be used to cause the container cap to emit a sound, vibration, or light signal to alert the user as to the location of the container cap, color shift the LED output to identify the owner, strobe to indicate a warning condition such as if medication was stored outside of prescribed temperature ranges, indicate whether or not the cap has been put on the correct bottle/container, convert the container cap display from counting up and display the time since last opened to a count-down time indicating the time remaining until the next dose is to be taken or otherwise remind the user that a dosage needs to be taken.

In addition to sending opening data, closing data, interval data, and other data collected by the one or more sensors, the container cap and external computer may also transmit or exchange data with or regarding pharmacy information, personal health records, hospital data, electronic medical records (EMR) and other databases to provide relevant information both on the device, personal communicators and web. This information for example can be combined with the databases of drug interaction, user experience, medical records and alert when multiple drugs, medical conditions or other conflicts or issues exist with potential effects.

The timer incorporated into the container cap of the present invention is preferably a digital timer with a display that is automatically activated and deactivated when the cap is affixed to, or removed from, the container, however, the timer may be analog without deviating from the scope of the invention.

The data collected by the sensors may be immediately and continuously transmitted by the transmitter, or it may be saved in the memory and then transmitted as part of a later transmission. If the data is sent immediately and continuously, it is still preferably saved in the memory.

Although the drawings show the portions of the container cap being distinct or integrated, it should be understood the container cap may be made out of fewer or more parts without deviating from the scope of the invention.

The parts, portions, and/or pieces of the container cap of the present invention may be assembled through any device or means, including, but not limited to a snap-fit assembly, glue, epoxy, ultrasonic welding, clips, fasteners, and/or friction, without deviating from the scope of the invention.

FIG. 1 is an illustration of a top exploded view of one embodiment of a container cap that records and transmits data. As shown in FIG. 1, the container cap 10 is preferably comprised of a protective cover 5 (which is preferably transparent over the display area), timer module 15, a sealing disk 17, a center post 19, center post spring 21, display 30, and housing 12. FIG. 1 shows how the housing 12 preferably protects and holds the timer module 15, which preferably contains the sensitive electronic portions of the container cap 10. The center post 19 preferably physically activates the activation switch (shown in FIG. 2), such that the container cap 10 knows when the container cap 10 is placed on a removed from container 200. FIG. 1 also shows how container cap 10 and container 200 are preferably a pharmaceutical cap and bottle or vial.

Figure 2:
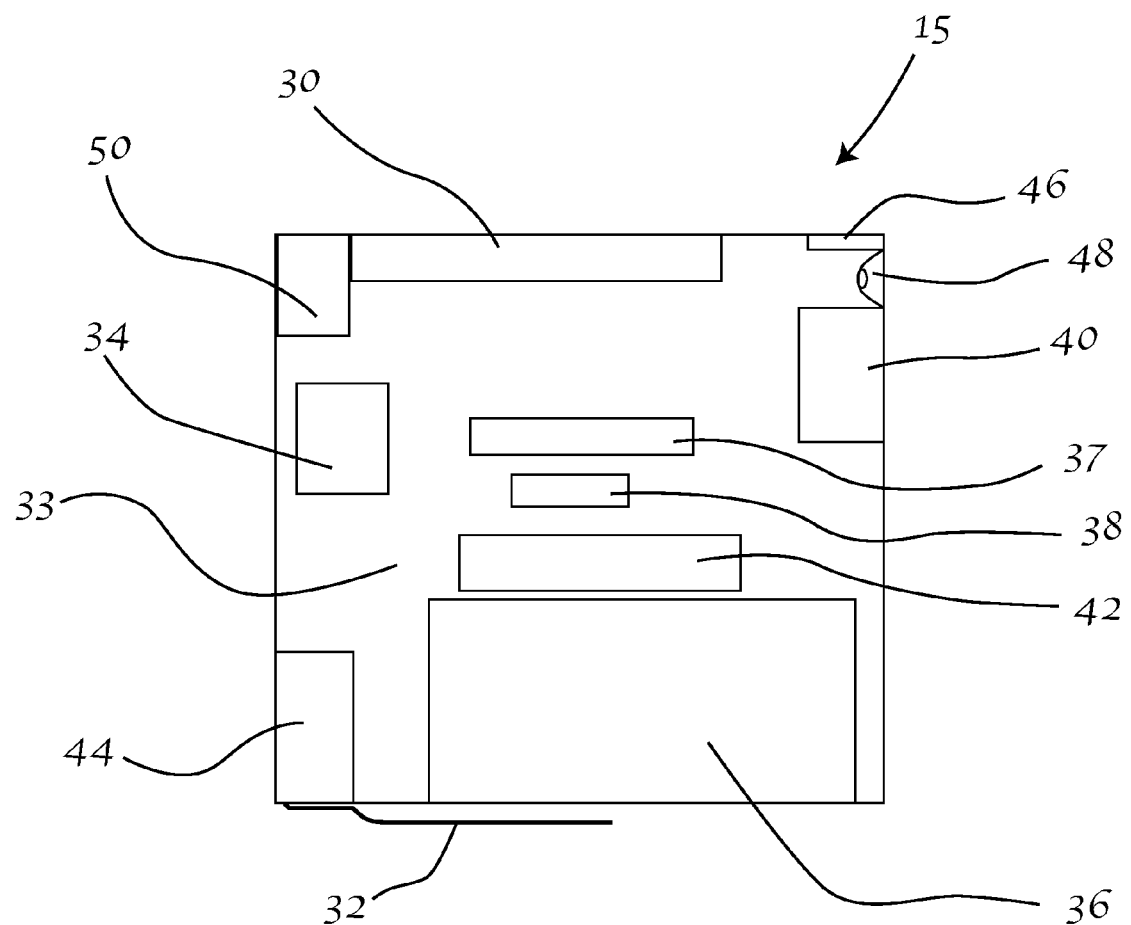
FIG. 2 is an illustration of a cross section view of one embodiment of the container cap that records and transmits data.

FIG. 2 is an illustration of a cross section view of one embodiment of the container cap that records and transmits data. As shown in FIG. 2, the timer module 15 preferably includes a display 30, which is typically a digital liquid crystal display, activation switch 32 (also called an activation sensor), timer 33, receiver 34, which may include an antenna, battery 36 (or other power source), a microcontroller 37, which may include a memory, an additional memory 38, a transmitter or transceiver 40, accelerometer 42, thermometer 44, one or more light sources 46; speaker 48; and a vibration device 50. Preferably activation sensor 32 and timer 33 capture for the microcontroller at least: (1) the interval between when the container cap 10 is placed on container 200 and when the container cap is then removed from container 200; and (2) the interval between when the container cap 10 is removed from container 200 and when the container cap is placed back on container 200. In this manner, the microcontroller and/or the external computer can determine the specific time references accurately, regardless of time zone changes. Alternatively, the sensor 32, timer 33, and microcontroller 37 may capture and store the opening and closing times based on a master clock, and then the intervals may be calculated by the microcontroller and/or the external computer.

Preferably, display 30 displays the duration of time, in hours and minutes, since the timer 33 was activated. In this manner, the user knows when he or she last took the medication within the container 200. When the activation switch 32 is disengaged, the timer 33 stops, and the display 30, which is preferably digital, stops counting and may cease to display any numbers. The timer 15 is again reset and re-started after the container cap 10 is re-engaged with container 200. Accordingly, it is very important that the activation switch 33 stay engaged until the container cap 10 is removed by the user, so that the user is not given a false duration of time since he or she last took the medicine and so that each opening and closing event are properly recorded by the microcontroller.

The present invention is streamlined and designed specifically for reliability, despite repeated engagement and disengagement of container cap 10 to container 200. The container and container cap may be child proof or have a non-child proof closure.

Preferably, the one or more light sources may be used, via color shifting, flashing, or strobing, to: a) identify one user/owner from another; b) alert the owner to a pending event, such as the time to take a medication has arrived or passed; and/or c) warn the user of a condition requiring attention, such as the fact that the medication has been stored outside prescribed temperature range, or it is time to reorder, etc.

In addition, the various sensors, alert devices, transmitters, transceivers, and receivers that are preferably part of the container cap 10 may be used to determine whether the container cap is on the correct bottle. Preferably, the container cap 10 and correct container would be radio frequency capable and enabled, such that the container cap 10 and correct container exchange an RFID (radio frequency identification). If the cap 10 is being put onto the wrong container, the RFID would not occur and the container cap 10 would then preferably alert the user to this fact. This alert could be, but is not limited to, a message on the display 30, a flash from the one or more light sources 46, a sound from speaker 48, or a vibration from vibrator 50. Alternatively, the alert may be performed when the cap 10 is put onto the correct bottle. In another alternative, the transmitter, transceiver, and/or receiver on the bottle may be under or part of a label on the bottle.

Figure 3:
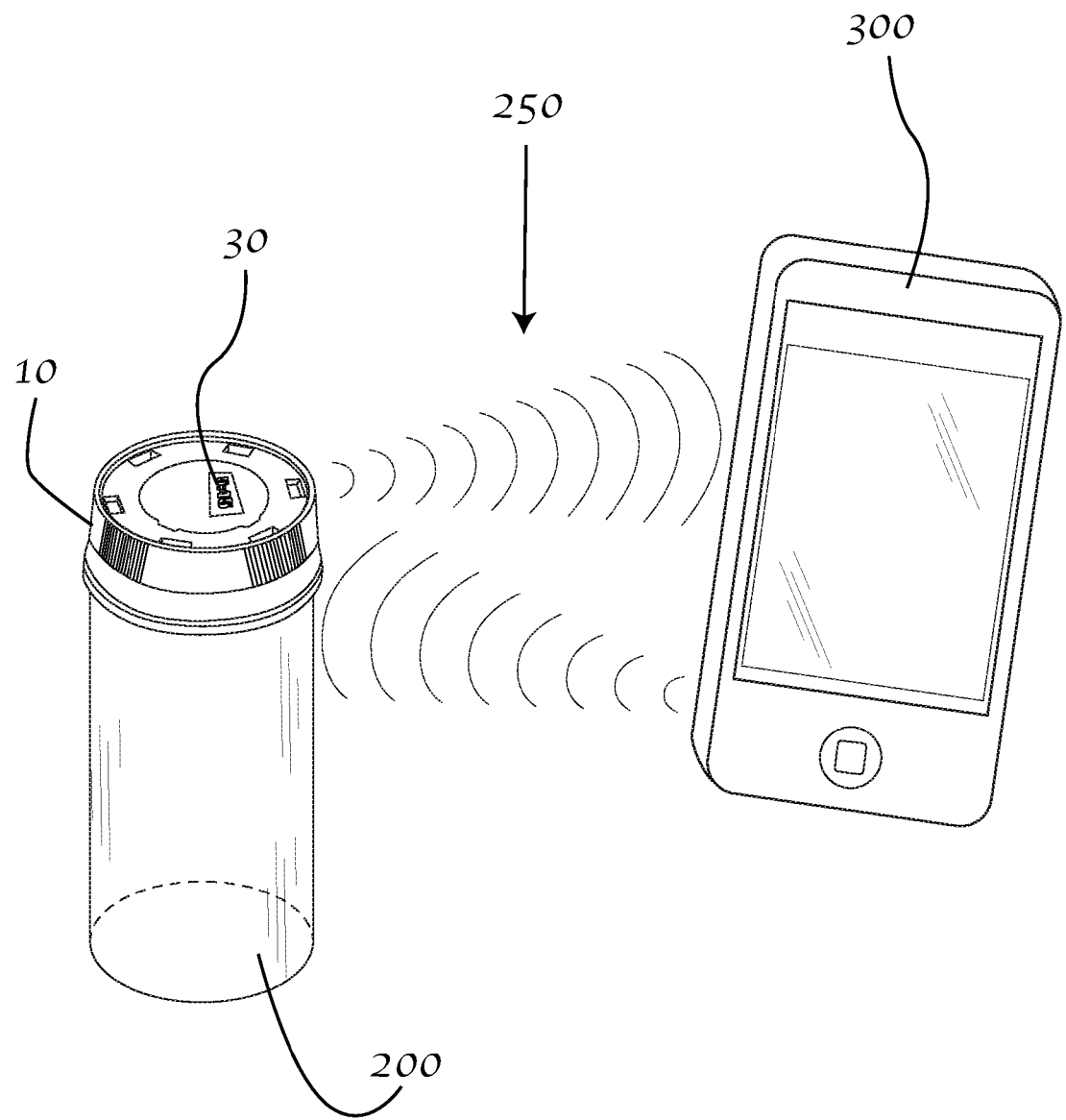
FIG. 3 is illustration of one embodiment of the container cap that records and transmits data and shows the container cap communicating with an external electronic data processing unit.

FIG. 3 is illustration of one embodiment of the container cap that records and transmits data and shows the container cap communicating with an external electronic data processing unit. As shown in FIG. 3, the container cap 10 preferably sends and receives transmissions 250 from an external electronic data processing unit 300, which is typically a smart phone, tablet computer, or other type of computer. Using the computer 300, the user is able to view data collected by the container cap 10, including the times that the container cap 10 was removed from the container 200 and the interval data between when the cap 10 was put on and then subsequently taken off the container 200, as well as data collected and transmitted by other sensors within the cap.

Figure 4:
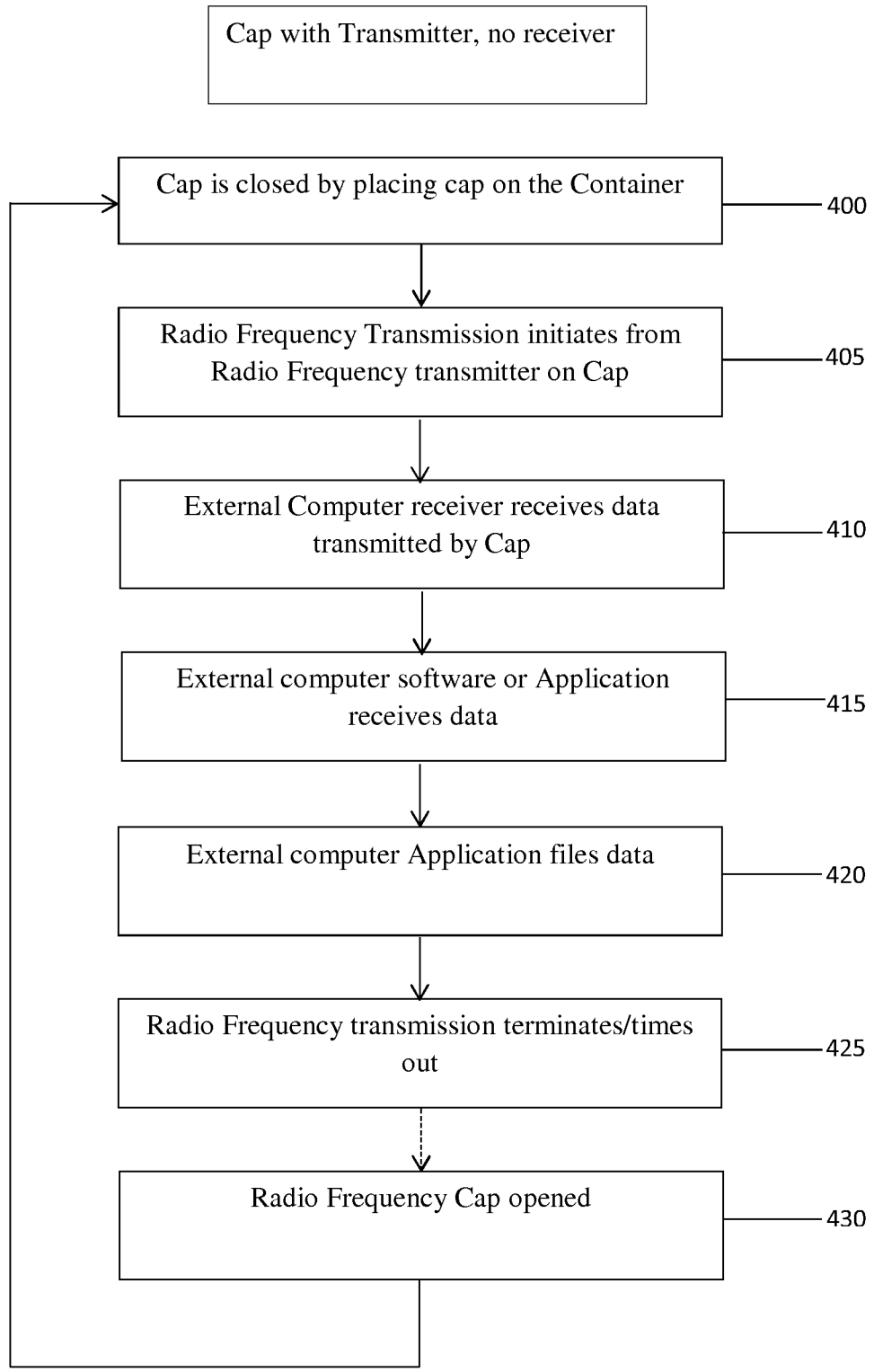
FIG. 4 is a flow block diagram of one embodiment of the container cap that records and transmits data.

FIG. 4 is a flow block diagram of one embodiment of a method for using a container cap that records and transmits data without a receiver. As shown in FIG. 4, one method for using the container cap of the present invention starts with closing the cap 400. The cap transmitter then initiates a transmission 405. Typically, this includes a beginning of transmission (BOT), an identifier, data from the memory, and then an end of transmission (EOT) signal. An external computer receives the transmission 410 and recognizes the identifier of the cap. The external computer application or software gets the transmission 415. The software or app. determines if the transmission is coming from a cap that is new, or one that has an existing record 420. If new a new record is created, if existing, the record is amended with any data that is new. The transmission of the cap stops or times out (after a preprogrammed interval) 425. Upon removal from the container a sensor in the cap captures the event in conjunction with the microcontroller 430. The time interval from closing to opening is recorded in the memory of the cap.

Figure 5:
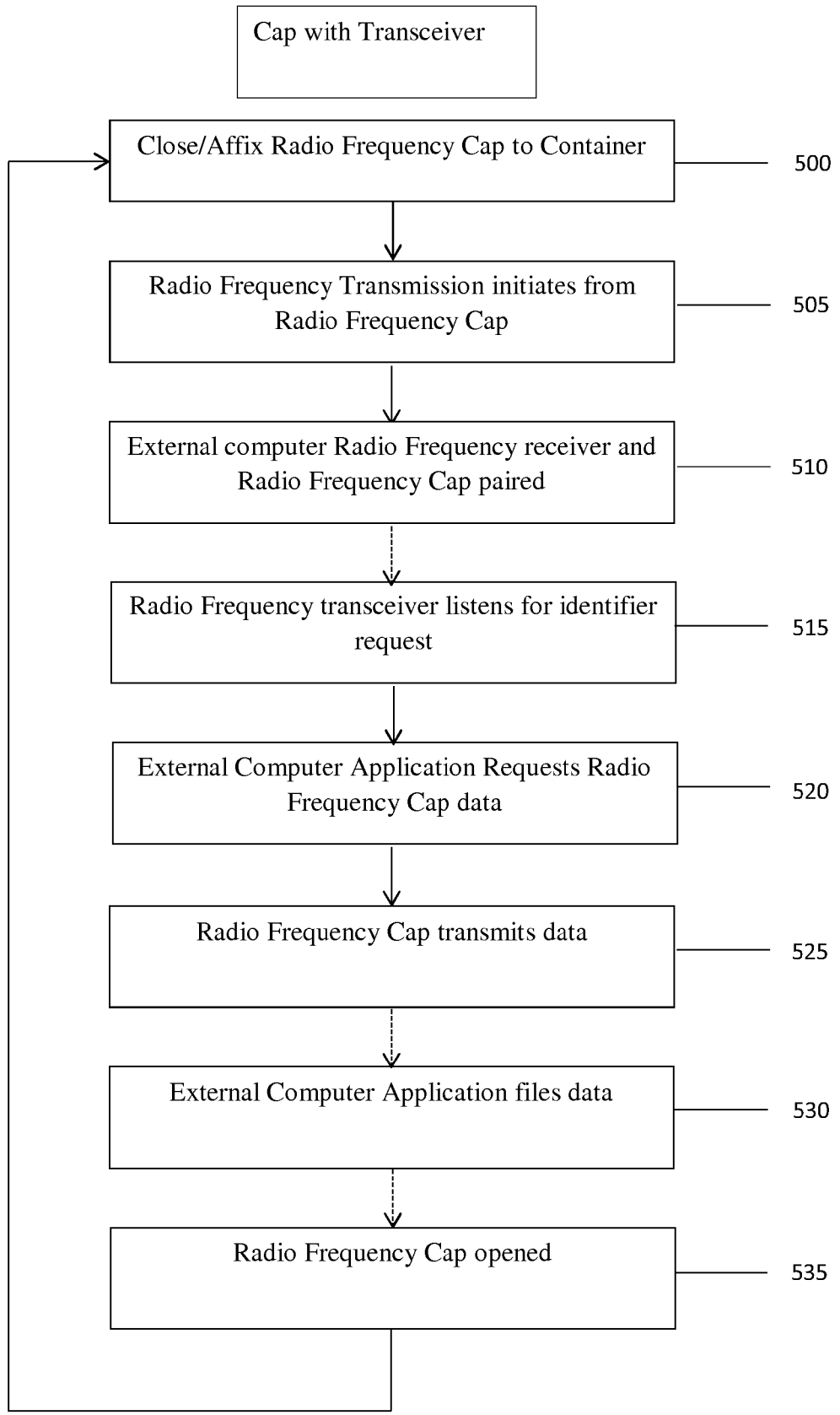
FIG. 5 is a second flow block diagram of one embodiment of the container cap that records and transmits data.

FIG. 5 is a flow block diagram of one embodiment of a method for using a container cap that records and transmits data with a transceiver, wherein the external electronic data processing unit requests transmission of data from the container cap. As shown in FIG. 5, another method starts with closing the cap 500. The cap initiates a transmission from the transceiver 505. The external computer recognizes the transmission and accepts the pairing event 510. The external computer application creates a record file. The transceiver on the cap listens for an identifier request from an external computer 515. This conserves the battery. The external computer requests that the cap communicate an identifier and open and close interval data 520. The cap transmits the BOT, event data and EOT until it receives acknowledgement of EOT receipt by the external computer 525. The cap then returns to listen only mode. The application of the external computer updates or creates records based on the contents of the transmission 530. The cap is opened, the event of which is captured by the sensors and microcontroller 535. The event and calculated interval information is determined and recorded.

Figure 6:
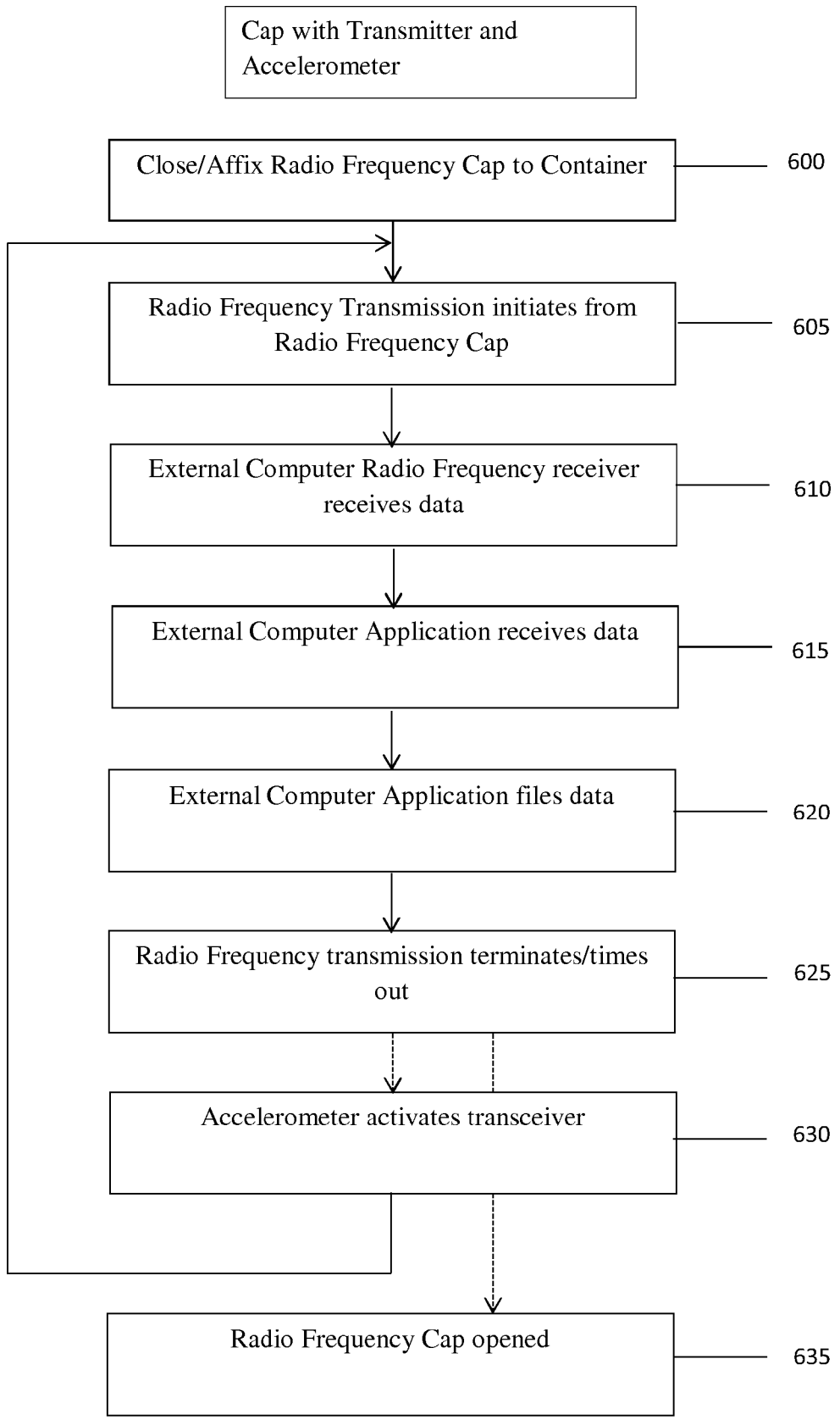
FIG. 6 is a third flow block diagram of one embodiment of the container cap that records and transmits data.

FIG. 6 is a flow block diagram of one embodiment of a method for using a container cap that records and transmits data without a receiver and with an accelerometer. The cap is closed, the event of which is captured by the sensors and microcontroller 600. The cap transmits, based on a closing event or an activation of the accelerometer, transmits a BOT, identifier, data, and an EOT 605. The external computer recognizes the identifier and accepts the transmission of data 610 and 615. The application on the external computer determines if the cap is new or an existing cap, and the record is saved, computed, and recorded accordingly 620. The transmission from the cap terminates or is timed out 625. The cap is picked up and manipulated, which is captured by the accelerometer, which causes the cap to start a transmission 630. The transmission may be tied to a specific programmed movement or any movement. The transmission is also started when the cap is opened 635.

Figure 7:
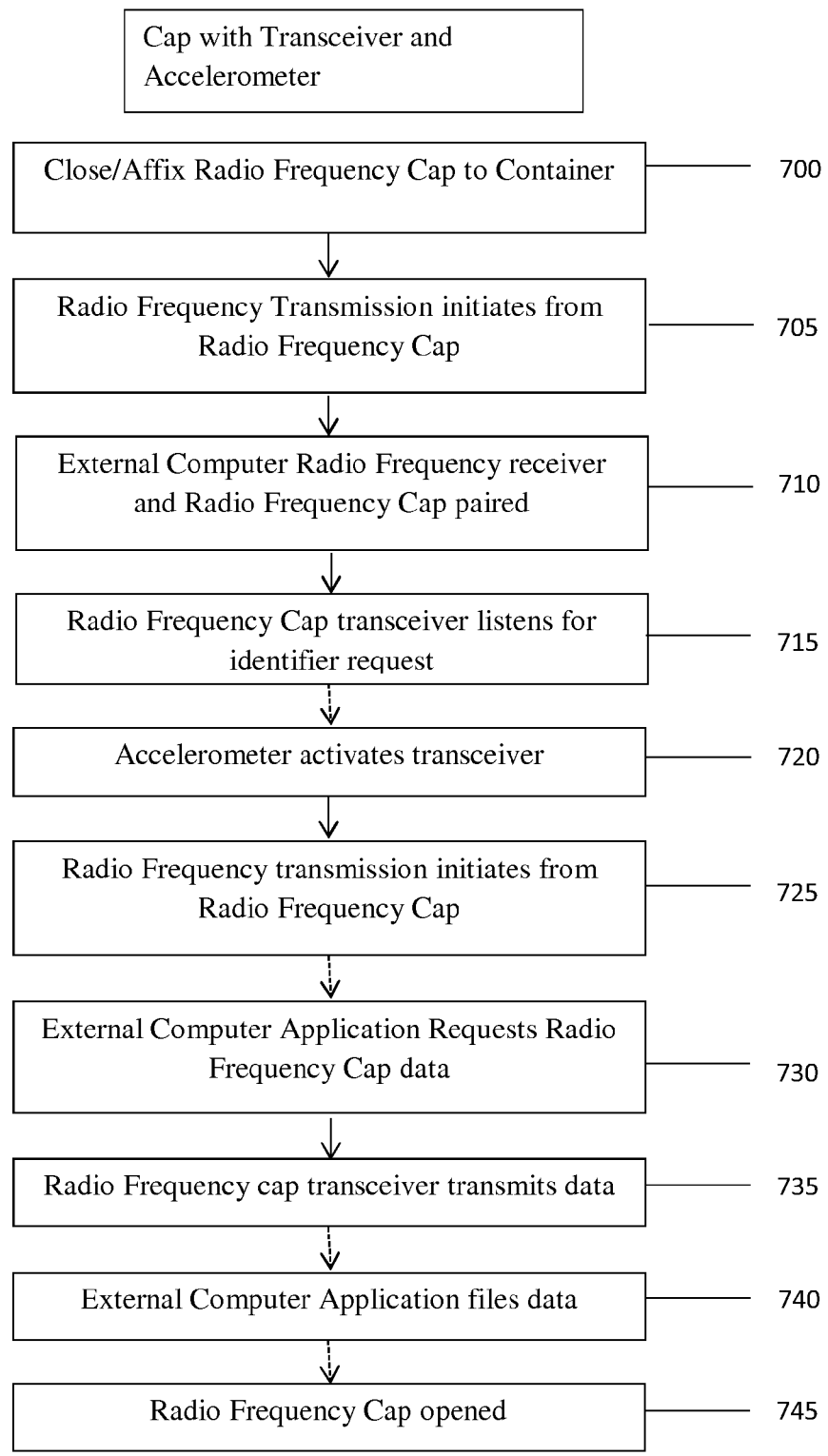
FIG. 7 is a fourth flow block diagram of one embodiment of the container cap that records and transmits data.

FIG. 7 is a flow block diagram of one embodiment of a method for using a container cap that records and transmits data with a transceiver and an accelerometer. The cap is closed, the event of which is captured by the sensors and microcontroller 700. The cap transceiver transmits a pairing event and generates a password on the display 705. The external computer recognizes the identifier and the user manually accepts the pairing by entering the password in the application of the external computer 710. The application on the external computer determines if the cap is new or an existing cap, and the record is saved, computed, and recorded accordingly. The transmission from the cap terminates or is timed out and listens for an identifier request 715. The cap is picked up and manipulated, which is captured by the accelerometer, which causes the cap to start a transmission 720, 725. The transmission may be tied to a specific programmed movement or any movement. The application in the external computer recognizes the cap and requests that the cap transmit an identifier and opening, closing, and interval data 730. The cap transmits the data, BOT, and EOT until the external computer acknowledges receipt 735. The cap then returns to listen only mode. The application of the external computer updates its records with the data received 740. Upon removal from the container the sensor and microcontroller capture this event 745. A transmission may or may not be sent upon the cap being opened.

The foregoing description of the preferred embodiment of the invention has been presented for the purposes of illustration and description. While multiple embodiments are disclosed, still other embodiments of the present invention will become apparent to those skilled in the art from the above detailed description, which shows and describes illustrative embodiments of the invention. As will be realized, the invention is capable of modifications in various obvious aspects, all without departing from the spirit and scope of the present invention. Accordingly, the detailed description is to be regarded as illustrative in nature and not restrictive. Also, although not explicitly recited, one or more embodiments of the invention may be practiced in combination or conjunction with one another. Furthermore, the reference or non-reference to a particular embodiment of the invention shall not be interpreted to limit the scope the invention. It is intended that the scope of the invention not be limited by this detailed description, but by the claims and the equivalents to the claims that are appended hereto.

What is claimed is:

1. A container cap that records and transmits data comprising:
    a container cap;
    wherein said container cap comprises: one or more sensors; a center post; a sealing disk; one or more microcontrollers; one or more transmitters; one or more power sources; and a housing portion;
    wherein said one or more sensors, said one or more microcontrollers, said one or more transmitters, and said one or more power sources are positioned within said container cap;
    wherein said center post is attached to an upper surface of said sealing disk and extends substantially perpendicularly away from said upper surface;
    wherein said one or more sensors comprise an activation switch;
    wherein said center post is configured to engage with said activation switch, such that when said container cap is placed on a container said one or more sensors are configured to automatically detect when said container cap is placed on said container;
    wherein said center post is configured to disengage from said activation switch, such that when said container cap is removed from said container said one or more sensors are configured to automatically detect when said container cap is removed from said container;
    wherein said one or more microcontrollers record when said container cap is opened by removing said container cap from said container and wherein said one or more microcontrollers record when said container cap is closed by placing said container cap on said container, such that a plurality of opening and closing interval data is created and stored in at least one memory;
    wherein said one or more transmitters transmits said plurality of opening and closing data to one or more external electronic data processing units;
    wherein said container cap further comprises a timer and a timer display;
    wherein said timer is activated when said container cap is closed and wherein said timer is reset when said container cap is opened;
    wherein said timer display displays an information regarding when said container cap was last closed;
    wherein a plurality of interval time duration data between a closing event and a next subsequent opening event and between an opening event and a next subsequent closing event, is computed by said one or more microcontrollers each time said container cap is opened and each time said container cap is closed and wherein said plurality of interval time duration data is stored in said at least one memory;
    wherein said container cap is further comprised of one or more alert devices;
    wherein said one or more alert devices create one or more alerts;
    wherein said one or more alerts are selected from the group of alerts consisting of: an auditory, a tactile, and a visual alert device; and
    wherein said one or more external electronic data processing units are configured to locate said container cap based on a signal strength of said one or more transmitters of said container cap.

2. The container cap of claim 1, wherein said one or more alert devices are alert devices selected from the group of alert devices consisting of: one or more light sources; a speaker; and a vibration device.

3. The container cap of claim 1, wherein said one or more alert devices alert a user regarding one or more reminders.

4. The container cap of claim 1, wherein said one or more alert devices alerts a user regarding one or more conditions regarding said container cap.

* * * * *